United States Patent [19]

Payne et al.

[11] Patent Number: 5,436,002
[45] Date of Patent: Jul. 25, 1995

[54] BACILLUS THURINGIENSIS ISOLATE PS201T6 TOXIN

[75] Inventors: Jewel Payne, Davis; Kenneth E. Narva, San Diego; Kendrick A. Uyeda, San Diego; Christine J. Stalder, San Diego, all of Calif.; Tracy E. Michaels, Ames, Iowa

[73] Assignee: Mycogen Corporation, San Diego, Calif.

[21] Appl. No.: 129,610

[22] Filed: Sep. 30, 1993

Related U.S. Application Data

[60] Continuation-in-part of Ser. No. 977,350, Nov. 17, 1992, abandoned, which is a division of Ser. No. 746,751, Aug. 21, 1991, Pat. No. 5,298,245, which is a continuation-in-part of Ser. No. 708,266, May 28, 1991, abandoned, which is a continuation-in-part of Ser. No. 647,399, Jan. 29, 1991, abandoned, and a continuation-in-part of Ser. No. 93,199, Jul. 15, 1993, abandoned.

[51] Int. Cl.$^6$ .................... A01N 63/00; C12N 15/32; A61K 38/16
[52] U.S. Cl. ............................ 424/93.461; 424/93.2; 536/23.71; 514/12; 435/320.1
[58] Field of Search .................... 435/69.1, 320.1; 424/93 L, 93 A, 93.461, 93.2; 536/23.71; 514/12

[56] References Cited

U.S. PATENT DOCUMENTS

| | | | |
|---|---|---|---|
| 4,448,885 | 5/1984 | Schnepf et al. | 435/172.3 |
| 4,467,036 | 8/1984 | Schnepf et al. | 435/172.3 |
| 4,797,276 | 1/1989 | Herrnstadt et al. | 424/84 |
| 4,849,217 | 7/1989 | Soares et al. | 424/93.461 |
| 4,853,331 | 8/1989 | Herrnstadt et al. | 435/252.1 |
| 4,918,006 | 4/1990 | Ellar et al. | 435/69.1 |
| 4,948,734 | 8/1990 | Edwards et al. | 435/252.5 |
| 5,064,648 | 11/1991 | Hickle et al. | 435/69.1 |
| 5,151,363 | 9/1992 | Payne | 435/252.5 |

FOREIGN PATENT DOCUMENTS

| | | |
|---|---|---|
| 0409438 | 7/1989 | European Pat. Off. |
| 0480762 | 4/1992 | European Pat. Off. |
| 9308692 | 5/1993 | WIPO |

OTHER PUBLICATIONS

Gaertner, F., L. Kim (1988) "Current Applied Recombinant DNA Projects" TIBTECH 6(4):S4–S7.

Gaertner, Frank (1990) "Cellular delivery systems for insecticidal proteins: living and non-living microorganisms" Controlled Delivery of Crop-Protection Agents 245–255.

Couch, Terry L. (1980) "Mosquito pathogenicity of *Bacillus thuringiensis* var. *israelensis*" Developments in Industrial Microbiology 22:61–76.

Beegle, Clayton, C. (1978) "Use of Entomogenous Bacteria in Agroecosystems" Developments in Industrial Microbiology 20:97–104.

Krieg, Von A. et al. (1983) "*Bacillus thuringiensis* var. *tenmebrionis*: ein neuer, gegenüber Larven von Coleopteren wirksamer Pathotyp" Z. ang. Ent. 96:500–508.

Höfte, H. and H. R. Whiteley (1989) "Insecticidal Crystal Proteins of *Bacillus thuringiensis*" Microbiological Reviews 53(2):242–255.

Feitelson, J. S., J. Paynbe, L. Kim (1992) "*Bacillus thuringiensis*: Insects and Beyond" Bio/Technology 10:271–275.

Schnepf, H. E., H. R. Whiteley (1981) "Cloning and expression of the *Bacillus thuringiensis* crystal protein gene in *Escherichia coli*" Proc. Natl. Acad. Sci. USA 78(5):2893–2897.

(List continued on next page.)

Primary Examiner—Che S. Chereskin
Attorney, Agent, or Firm—Saliwanchik & Saliwanchik

[57] ABSTRACT

Disclosed and claimed are toxins produced by novel *Bacillus thuringiensis* isolates designated B.t. PS92J, B.t. PS196S1, B.t. PS201L1, and B.t. PS201T6, which have dipteran and/or corn rootworm activity. Thus, the isolates, or mutants thereof, can be used to control such pests. Further, claimed are novel genes encoding these δ-endotoxins, which can be expressed in other hosts. Expression of the δ-endotoxins in such hosts results in the control of susceptible insect pests in the environment of such hosts.

8 Claims, 1 Drawing Sheet

OTHER PUBLICATIONS

Goldberg, L. J., J. Margalit (1977) "A bacterial spore demonstrating rapid larvicidal activity aginst *Anopheles, Sergentii, Uranotaenia Unguiculata, culex univitattus, aedes aegypti* and *culex pipiens*" Mosquito News 37:355–358.

Padua, Leodegario E. et al. (1984) "Isolation of *Bacillus thuringiensis* Strain (serotype 8a:8b) Highly and Selectively Toxic against Mosquito Larvae" J. Invertebrate Pathology 44:12–17.

Temeyer, Kevin B. (1990) "Potential of *Bacillus thuringiensis* for Fly Control" 5th International Colloquium on Invertebrate Pathology and Microbial Control, Society for Invertebrate Pathology 352–356.

Metcalf, G., W. Flint (1962) "Destructive and Useful Insects-Their Habits and Control" 1030–1035.

Parrella, M. P. (1987) "Biology of *Liriomyza*" Ann. Rev. Entomol 32:210–224.

Hespenheide, H. A. (1991) "Bionomics of Leaf–Mining Insects" Annu. Rev. Entomol.36:535–560.

Metcalf, Robert L. (1986) "Methods for the Study of Pest *Diabrotica*" vii–xv.

Thorne, et al. (1986) Journal of Bacteriology 166(3):801–811.

Donovan, et al. (Oct. 1988) Journal of Bacteriology 170 (10):4732–4738.

Sekar (1986) Biochem Biophys Res Commun. 137(2):748–751.

Ahmad, et al. (1989) FEMS Microbiology Lett 59:197–202.

A. Protein standard
B. *B.t.* PS192N1
C. *B.t.* PS123D1
D. *B.t.* PS71M3
E. Protein standard
F. *B.t.* PS201T6
G. *B.t.* PS201L1
H. *B.t.* PS196S1
I. *B.t.* PS92J
J. Protein standard

BACILLUS THURINGIENSIS ISOLATE PS201T6 TOXIN

CROSS-REFERENCE TO A RELATED APPLICATION

This is a continuation-in-part of application Ser. No. 07/977,350, filed Nov. 17, 1992, now abandoned, which is a division of application Ser. No. 07/746,751, filed Aug. 21, 1991, now U.S. Pat. No. 5,298,245, which is a continuation-in-part of application Ser. No. 07/708,266 filed May 28, 1991, now abandoned, which is a continuation-in-part of application Ser. No. 07/547,399 filed Jan. 29, 1991, now abandoned. This is also a continuation-in-part of application Ser. No. 08/093,199, filed Jul. 15, 1993, now abandoned.

BACKGROUND OF THE INVENTION

The soil microbe *Bacillus thuringiensis* (B.t.) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain B.t. toxin genes have been isolated and sequenced, and recombinant DNA-based B.t. products have been produced and approved for use. In addition, with the use of genetic engineering techniques, new approaches for delivering B.t. endotoxins to agricultural environments are under development, including the use of plants genetically engineered with endotoxin genes for insect resistance and the use of stabilized intact microbial cells as B.t. endotoxin delivery vehicles (Gaertner, F. H., L. Kim [1988] TIBTECH 6:S4–7). Thus, isolated B.t. endotoxin genes are becoming commercially valuable.

Until the last ten years, commercial use of B.t. pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystal called a δ-endotoxin which is toxic to the larvae of a number of lepidopteran insects.

In recent years, however, investigators have discovered B.t. pesticides with specificities for a much broader range of pests. For example, other species of B.t., namely *israelensis* and *tenebrionis* (a.k.a. B.t. M-7, a.k.a. B.t. *san diego*), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. *israelensis*," *Developments in Industrial Microbiology* 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) *Z. ang. Ent.* 96:500–508, describe *Bacillus thuringiensis* var. *tenebrionis*, which is reportedly active against two beetles in the order Coleoptera. These are the Colorado potato beetle, *Leptinotarsa decemlineata*, and *Agelastica alni*.

Recently, new subspecies of B.t. have been identified, and genes responsible for active δ-endotoxin proteins have been isolated (Höfte, H., H. R. Whiteley [1989] *Microbiological Reviews* 52(2):242–255). Höfte and Whiteley classified B.t. crystal protein genes into 4 major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271–275).

The cloning and expression of a B.t. crystal protein gene in *Escherichia coli* has been described in the published literature (Schnepf, H. E., H. R. Whitely [1981] *Proc. Natl. Acad. Sci. USA* 78:2893–2897). U.S. Pat. Nos. 4,448,885 and 4,467,036 both disclose the expression of B.t. crystal protein in *E. coli*. U.S. Pat. Nos. 4,797,276 and 4,853,331 disclose *B. thuringiensis* strain *san diego* (a.k.a. B.t. *tenebrionis*, a.k.a. M-7) which can be used to control coleopteran pests in various environments. U.S. Pat. No. 4,918,006 discloses B.t. toxins having activity against Dipterans. U.S. Pat. No. 4,849,217 discloses B.t. isolates which have activity against the alfalfa weevil. U.S. Pat. Nos. 5,151,363 and 4,948,734 disclose certain isolates of B.t. which have activity against nematodes. As a result of extensive research and investment of resources, other patents have issued for new B.t. isolates and new uses of B.t. isolates. However, the discovery of new B.t. isolates and new uses of known B.t. isolates remains an empirical, unpredictable art.

Dipteran insects are serious nuisances as well as being vectors of many human and animal diseases such as malaria, onchocerciasis, equine encephalitis, and dog heartworm. The activity spectrum of B.t. δ-endotoxins to insects of the order Diptera includes activity against mosquitoes as well as black flies. See Couch, supra; Beegle, supra.

The two varieties of B.t. known to kill mosquitos and blackflies are B.t. *israelensis* (B.t.i.) (Goldberg, L. J., J. Margalit [1977] *Mosquito News* 37:355–358) and B.t. *morrisoni* (B.t.m.) (Padua, L. E., M. Ohba, K. Aizawa [1984] *J. Invertebrate Pathology* 44:12–17). These B.t. are not harmful to non-target organisms (Mulla, M. S., B. A. Federici, H. A. Darwazeh [1982] *Environmental Entomology* 11:788–795), and play an important role in the integrated management of dipteran pests. They are safe to use in urban areas, and can be used in aquatic environments without harm to other species.

Dipteran pests are also a major problem in the poultry and cattle industries. The horn fly, a serious cattle pest, is killed by B.t. in the larval stages (Temeyer, K. B. [1990] "Potential of *Bacillus thuringiensis* for fly control," *Fifth International Colloquium on Invertebrate Pathology and Microbial Control, Society for Invertebrate Pathology*, 352–356). European Patent Application 90307204.9 (Publication No. 0 409 438) discloses *Bacillus thuringiensis* dipteran-active isolates PS71M3 and PS123D1.

Flies are an abundant species that can be found almost everywhere. They usually occur in such large numbers as to constitute a nuisance. The majority of the Diptera are considered pests and are of economic importance. A number of adult species are blood-sucking and cause irritation to man and domestic animals. Others are scavenging flies that mechanically transmit organisms and pathogens that contaminate food. Both types of flies are important vectors of disease, such as malaria, yellow fever, filariasis, sleeping sickness, typhoid fever, and dysentery. Larvae of a few species are pests of major agriculture crops. The larvae can feed on all parts of the plant such as seeds, roots, leaves and fruits. Larvae of certain species feed on fungus causing damage to mushroom production. Larvae can irritate domestic animals when they develop in the animal. Both the adults and larval forms of dipterans are considered pests to man and in agriculture.

House flies (family Museidae) are an important pest from the order Diptera. They are considered a nuisance and are vectors of human and animal diseases. Their habits of walking and feeding on garbage and excrement and on the human person and food make them ideal agents for the transfer of disease (Metcalf, C. and Flint, W. 1962. *Destructive and Useful Insects*, McGraw-Hill Book Co., N.Y., pp. 1030–1035). House flies are also a pest to animals and transmit disease through open wounds. The family Muscidae also includes the little house fly, face fly, stable fly, and horn fly, all of which are pests of livestock. These species are pests of cattle, poultry, horses and other types of livestock. They breed in manure and decaying straw located near the animals. The horn and stable flies are biting flies which cause stress to dairy cattle reducing milk production. The family Muscidae is considered an economic problem domestically and worldwide.

Leafmining flies cause damage and yield loss to economically important crops such as potatoes, tomatoes and celery. Dipteran leafminers are also considered a major pest in the ornamental flower industry (Parrella, M. P. [1987] "Biology of Liriomyza," *Ann. Rev. Entomol.* 32:201–224). The most common leafminers are found in the family Agromyzidae although the families Anthomyiidae, Drosophilidae and Ephydridae also contain leafmining flies (Hespenheide, H. A. [1991] "Bionomics of leafmining insects," *Ann. Rev. Entomolo.* 36:535–60). Flies in the genus Liriomyza (also known as serpentine leafminers) are particularly important because of their worldwide distribution, polyphagous nature and resistance to insecticides. In the state of California, the chrysanthemum industry lost approximately 93 million dollars to *Liriomyza trifolii* between the years of 1981–1985.

There are also dipteran pests of plants, such as Hessian fly, Medfly, and Mexfly, for which a B.t. product would be very valuable.

Another serious pest to plants is the corn rootworm. The corn rootworm is a coleopteran pest. Extensive damage occurs to the United States corn crop each year due to root feeding by larvae of corn rootworm (Diabrotica spp.). Three main species of corn rootworm, Western corn rootworm (*Diabrotica virgifera virgifera*), Northern corn rootworm (*Diabrotica barberi*), and Southern corn rootworm (*Diabrotica undecimpunctata howardi*) cause varying degrees of damage to corn in the United States. It has been estimated that the annual cost of insecticides to control corn rootworm and the annual crop losses caused by corn rootworm damage exceeds a total of $1 billion in the United States each year (Meycalf, R. L. [1986] in *Methods for the Study of Pest Diabrotica*, Drysan, J. L. and T. A. Miller [Eds.], Springer-Verlag, New York, N.Y., pp. vii–xv). Approximately $250 million worth of insecticides are applied annually to control corn rootworms in the United States. In the Midwest, $60 million and $40 million worth of insecticide were applied in Iowa and Nebraska, respectively, in 1990. Even with insecticide use, rootworms cause about $750 million worth of crop damage each year, making them the most serious corn insect pest in the Midwest.

The life cycle of each Diabrotica species is similar. The eggs of the corn rootworm are deposited in the soft. Newly hatched larvae (the first instar) remain in the ground and feed on the smaller branching corn roots. Later instars of Western and Northern corn rootworms invade the inner root tissues that transport water and mineral elements to the plants. In most instances, larvae migrate to feed on the newest root growth. Tunneling into roots by the larve results in damage which can be observed as brown, elongated scars on the root surface, tunneling within the roots, or varying degrees of pruning. Plants with pruned roots usually dislodge after storms that are accompanied by heavy rains and high winds. The larvae of Southern corn rootworm feed on the roots in a similar manner as the Western and Northern corn rootworm larvae. Southern corn rootworm larvae may also feed on the growing point of the stalk while it is still near the soil line, which may cause the plant to wilt and die.

After feeding for about 3 weeks, the corn rootworm larvae leave the roots and pupate in the soil. The adult beetles emerge from the soil and may feed on corn pollen and many other types of pollen, as well as on corn silks. Feeding on green silks can reduce pollination level, resulting in poor grain set and poor yield. The Western corn rootworm adult also feeds upon corn leaves, which can slow plant growth and, on rare occasions, kill plants of some corn varieties.

Current methods for controlling corn rootworm damage in corn are limited to the use of crop rotation and insecticide application. However, economic demands on the utilization of farmland restrict the use of crop rotation. In addition, an emerging two-year diapause (or overwintering) trait of Northern corn rootworms is disrupting crop rotations in some areas.

The use of insecticides to control corn rootworm also has several drawbacks. Continual use of insecticides has allowed resistant insects to evolve. Situations such as extremely high populations of larve, heavy rains, and improper calibration of insecticide application equipment can result in poor control. Insecticide use often raises environmental concerns such as contamination of soil and of both surface and underground water supplies. Working with insecticides may also pose hazards to the persons applying them.

BRIEF SUMMARY OF THE INVENTION

The subject invention concerns toxins, and genes encoding toxins, obtainable from *Bacillus thuringiensis* isolates. These toxins have advantageous activity against dipteran and coleopteran pests. Specifically, *Bacillus thuringiensis* isolates and toxins have been found to be active against the yellow fever mosquito, *Aedes aegypti*, house fly, *Musca domestica*, leafmining flies *Liriomyza trifolii*, and Western corn rootworm.

More specifically, the invention concerns novel B.t. isolates designated B.t. PS92J, B.t. PS196S1, B.t. PS201L1, and B.t. PS201T6, and mutants thereof, and novel delta endotoxin genes obtainable from these B.t. isolates which encode proteins which are active against dipteran and/or coleopteran pests.

When controlling Dipteran pests, the *Bacillus thuringiensis* isolates, or toxins therefrom, can be utilized as a spray for litter, manure, water, plants and other surfaces. They can also be used as a feed-through for domesticated animals and livestock. Transgenic plants and seeds can be used for control of stem, leaf, and seed feeding maggots. Seeds can also be treated with a slurry of the isolate or toxin therefrom.

For the control of corn rootworm, transgenic plants are the preferred method of delivery. Application to the soil can also be done.

Still further, the invention includes the treatment of substantially intact B.t. cells, or recombinant cells containing the genes of the invention, to prolong the pesticidal activity when the substantially intact cells are applied to the environment of a target pest. Such treatment can be by chemical or physical means, or a combination of chemical and physical means, so long as the technique does not deleteriously affect the properties of the pesticide, nor diminish the cellular capability in protecting the pesticide. The treated cell acts as a protective coating for the pesticidal toxin. The toxin becomes available to act as such upon ingestion by a target pest.

BRIEF DESCRIPTION OF THE SEQUENCES

Figure 1:
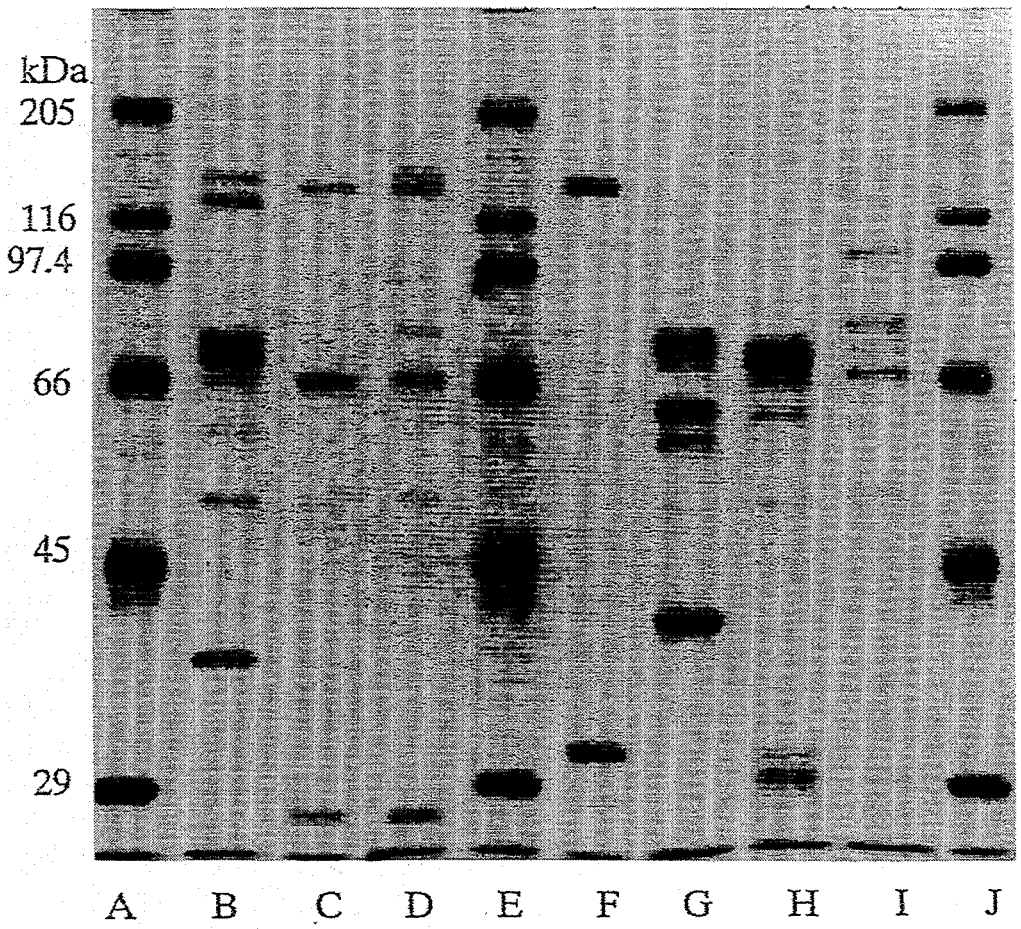
FIG. 1 is a photograph of a standard SDS polyacrylamide gel showing alkali-soluble proteins of mosquito-active B.t. strains.

SEQ ID NO. 1 is an oligonucleotide probe used according to the subject invention.

SEQ ID NO. 2 is a B.t. primer used according to the subject invention.

SEQ ID NO. 3 is a 3' reverse oligonucleotide primer used according to the subject invention.

SEQ ID NO. 4 is a gene-specific primer used according to the subject invention.

SEQ ID NO. 5 is a promoter sequence-primer used according to the subject invention.

SEQ ID NO. 6 is the nucleotide sequence encoding the 30 kDa 201T6 toxin.

SEQ ID NO. 7 is the deduced amino acid sequence of the 30 kDa 201T6 toxin.

SEQ ID NO. 8 is the amino acid sequence of a truncated 201T6 toxin of about 25 kDa.

SEQ ID NO. 9 is the N-terminal amino acid sequence of the 30 kDa 201T6 toxin.

SEQ ID NO. 10 is an oligonucleotide probe used according to the subject invention.

DETAILED DISCLOSURE OF THE INVENTION

The subject invention concerns novel B.t. isolates, as well as B.t. toxins and genes which encode these toxins. The B.t. isolates and their toxins have been found to have dipteran and/or coleopteran activity. All of the isolates have dipteran activity and certain isolates as described herein also have coleopteran activity.

Specific *Bacillus thuringiensis* isolates useful according to the subject invention have the following characteristics in their biologically pure form:

TABLE 1

Characteristics distinguishing B.t. PS92J, B.t. PS196S1, B.t. PS201L1, and B.t. PS201T6 from each other and from known mosquito-active strains

| Serovar | | Inclusion | Protein sizes* (kDa) |
|---|---|---|---|
| Known Strains | | | |
| B.t. PS71M3 | 8a8b, morrisoni | amorphic | 142, 133 doublet, 67, 27 |
| B.t. PS123D1 | 14, israelensis | amorphic | 133, 67, 27 |

TABLE 1-continued

Characteristics distinguishing B.t. PS92J, B.t. PS196S1, B.t. PS201L1, and B.t. PS201T6 from each other and from known mosquito-active strains

| Serovar | | Inclusion | Protein sizes* (kDa) |
|---|---|---|---|
| B.t. PS192N1 | 19, tochigiensis | amorphic | 140, 122, 76, 72, 38 |
| New Strains | | | |
| B.t. PS92J | new serovar | amorphic | 102, 81, 67 |
| B.t. PS196S1 | 10, darmstadiensis | amorphic | 73, 69, 29 |
| B.t. PS201L1 | no reaction | amorphic | 75 triplet, 62, 40 |
| B.t. PS201T6 | 24, neoleonensis | elliptical & bipyramidal | 133, 31 |

*As estimated on SDS gels

The novel B.t. isolates of the invention, and mutants thereof, can be cultured using standard known media and fermentation techniques. Upon completion of the fermentation cycle, the bacteria can be harvested by first separating the B.t. spores and crystals from the fermentation broth by means well known in the art. The recovered B.t. spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains. The novel B.t. isolates, and mutants thereof, can be used to control dipteran pests and/or corn rootworm. As used herein, reference to corn rootworm refers to its various life stages including the larval stage.

The cultures of the subject invention were deposited in the Agricultural Research Service Patent Culture Collection (NRRL), Northern Regional Research Center, 1815 North University Street, Peoria, Ill. 61604 USA.

| Culture | Accession No. | Deposit date |
|---|---|---|
| *Bacillus thuringiensis* PS92J | NRRL B-18747 | January 9, 1991 |
| *Bacillus thuringiensis* PS196S1 | NRRL B-18748 | January 9, 1991 |
| *Bacillus thuringiensis* PS201L1 | NRRL B-18749 | January 9, 1991 |
| *Bacillus thuringiensis* PS201T6 | NRRL B-18750 | January 9, 1991 |
| *E. coli* NM522 (pMYC 2362) | NRRL B-21018 | December 2, 1992 |
| *E. coli* NM522 (pMYC 2357) | NRRL B-21017 | December 2, 1992 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. These deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing a culture. The depositor acknowledges the duty to replace a deposit should the depository be unable to furnish a sample when requested, due to the condition of a deposit. All restrictions on the availability to the public of the subject culture deposits will be irrevocably removed upon the granting of a patent disclosing them.

Genes and toxins

The genes and toxins useful according to the subject invention include not only the full length sequences disclosed but also fragments of these sequences, variants, mutants, and fusion proteins which retain the characteristic pesticidal activity of the toxins specifically exemplified herein. As used herein, the terms "variants" or "variations" of genes refer to nucleotide sequences which code for the same toxins or which code for equivalent toxins having pesticidal activity. As used herein, the term "equivalent toxins" refers to toxins having the same or essentially the same biological activity against the target pests as the claimed toxins.

It should be apparent to a person skilled in this art that genes coding for active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from B.t. isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other B.t. toxins. These antibodies can then be used to specifically identify equivalent toxins with the characteristic activity by immunoprecipitation, enzyme linked immunosorbent assay (ELISA), or Western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the an to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and genes of the subject invention is through the use of oligonucleotide probes. These probes are nucleotide sequences having a means for detection. As is well known in the art, if the probe molecule and nucleic acid sample hybridize by forming a strong bond between the two molecules, it can be reasonably assumed that the probe and sample have substantial homology. The probe's means of detection provides a means for determining in a known manner whether hybridization has occurred. Such a probe analysis provides a rapid method for identifying toxin-encoding genes of the subject invention. The nucleotide segments which are used as probes according to the invention can be synthesized by use of DNA synthesizers using standard procedures. These nucleotide sequences can also be used as PCR primers to amplify genes of the subject invention.

Certain toxins of the subject invention have been specifically exemplified herein. Since these toxins are merely exemplary of the toms of the subject invention, it should be readily apparent that the subject invention further comprises variant or equivalent toxins (and nucleotide sequences coding for equivalent toxins) having the same or essentially the same pesticidal activity of the exemplified toxins. These equivalent toxins can have amino acid homology with an exemplified toxin. This amino acid homology will typically be greater than 75%, preferably be greater than 90%, and most preferably be greater than 95%. The amino acid homology will be highest in certain critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 2 provides a listing of examples of amino acids belonging to each class.

TABLE 2

| Class of Amino Acid | Examples of Amino Acids |
|---|---|
| Nonpolar | Ala, Val, Leu, De, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions, which are described above.

Recombinant hosts

The toxin-encoding genes harbored by the isolates of the subject invention can be introduced into a wide variety of microbial or plant hosts. Expression of the toxin gene results, directly or indirectly, in the intracellular production and maintenance of the pesticide. With suitable microbial hosts, e.g., Pseudomonas, the microbes can be applied to the situs of the pest, where they will proliferate and be ingested. The result is a control of the pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans*. Of particular interest are the pigmented microorganisms.

A wide variety of ways are available for introducing a B.t. gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of cells

As mentioned above, B.t. or recombinant cells expressing a B.t. toxin can be treated to prolong the toxin activity and stabilize the cell for application to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., *Animal Tissue Techniques*, W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bio-availability or bioactivity of the toxin.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations

Formulated bait granules containing an attractant and spores and crystals of the B.t. isolates, or recombinant microbes comprising the genes obtainable from the B.t. isolates disclosed herein, can be applied to the soil. Formulated product can also be applied as a seed-coating or root treatment or total plant treatment at later stages of the crop cycle. These formulations are particularly relevant for the control of corn rootworm. Product can be formulated as a feedthrough for domesticated animals and livestock. B.t. isolates and recombinant microbes can be treated as described above such that they pass through the animals intact and are secreted in the feces, where they are ingested by a variety of pests, thereby offering a means for controlling such pests.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the dipteran or corn rootworm pest, e.g., soil, manure, water, by spraying, dusting, sprinkling, or the like.

Mutants

Mutants of the novel isolates of the invention can be made by procedures well known in the art. For example, an asporogenous mutant can be obtained through ethylmethane sulfonate (EMS) mutagenesis of a novel isolate. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell treatment process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is placed in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

Example 1

Culturing of the Novel B.t. Isolates

A subculture of the novel B.t. isolates, or mutants thereof, can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

Example 2

Purification and Amino Acid Sequencing

A *Bacillus thuringiensis* (B.t.) can be cultured as described in Example 1 or by using other standard media and fermentation techniques well known in the art. The delta endotoxin can be isolated and purified by harvesting toxin protein inclusions by standard sedimentation centrifugation. The recovered protein inclusions can be partially purified by sodium bromide (28–38%) isopycnic gradient centrifugation (Pfannenstiel, M. A., E. J. Ross, V. C. Kramer, K. W. Nickerson [1984] FEMS *Microbiol. Lett.* 21:39). Thereafter the individual toxin proteins can be resolved by solubilizing the crystalline protein complex in an alkali buffer and fractionating the individual proteins by DEAE-sepharose CL-6B (Sigma Chem. Co., St. Louis, Mo.) chromatography by stepwise increments of increasing concentrations of an NaCl-containing buffer (Reichenberg, D., in *Ion Exchangers in Organic and Biochemistry* [C. Calmon and T. R. E. Kressman, eds.], Interscience, New York, 1957).

Fractions containing the 30 kDa 201T6 toxin were bound to PVDF membrane (Millipore, Bedford, Mass.) by Western blotting techniques (Towbin, H., T. Staehelin, K. Gordon [1979] *Proc. Natl. Acad. Sci. USA* 76:4350) and the N-terminal amino acid sequence was determined by the standard Edman reaction with an automated gas-phase sequenator (Hunkapiller, M. W., R. M. Hewick, W. L. Dreyer, L. E. Hood [1983] *Meth. Enzymol.* 91:399). The sequence obtained was: $NH_2$—MKESIYYNEE—$CO_2H$ (SEQ ID NO. 9).

From this sequence data on oligonucleotide probe was designed by utilizing a codon frequency table assembled from available sequence data of other B.t. toxin genes. The oligonucleotide probe corresponding to the N-terminal amino acid sequence of SEQ ID NO. 9 is 5'-ATG AAA GAA (T/A) (G/C) (T/A) AT(T/A) TAT TAT ATT GAA GA-3' (SEQ ID NO. 10). Probes can be synthesized on an Applied Biosystems, Inc. DNA synthesis machine.

Example 3

Molecular Cloning and Expression of Toxin Genes from *Bacillus thuringiensis* Strain PS201T6

Total cellular DNA was prepared from *Bacillus thuringiensis* (B.t.) PS201T6 cells grown to an optical density, at 600 nm, of 1.0. Cells were pelleted by centrifugation and resuspended in protoplast buffer (20 mg/ml lysozyme in 0.3M sucrose, 25 mM Tris-Cl (pH 8.0), 25 mM EDTA). After incubation at 37° C. for 1 hour, protoplasts were lysed by two cycles of freezing and thawing. Nine volumes of a solution of 0.1M NaCl, 0.1% SDS, 0.1M Tris-Cl were added to complete lysis. The cleared lysate was extracted twice with phenol:-chloroform (1:1). Nucleic acids were precipitated with two volumes of ethanol and pelleted by centrifugation. The pellet was resuspended in TE buffer and RNase was added to a final concentration of 50 μg/ml. After incubation at 37° C. for 1 hour, the solution was extracted once each with phenol:chloroform (1:1) and TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE buffer.

RFLP analyses were performed by standard hybridization of Southern blots of PS201T6 DNA digested with various restriction endonucleases. An oligonucleotide probe deduced from the amino acid sequence of the 30 kDa toxin was used to detect the gene encoding this polypeptide. The sequence of this probe was: 5'-GACTGGATCC ATGAAAGAA(T or A) (G or C)(T or A)AT(T or A)TATTA TAATGAAGA-3' (SEQ ID NO. 1). This probe was mixed at four positions and contained a 5' BamHI cloning site. Hybridizing bands included an approximately 4.0 kbp EcoRI fragment and an approximately 2.7 kbp EcoRV fragment.

A 285 bp probe for detection of the 130 kDa toxin gene was obtained by polymerase chain reaction (PCR) amplification from 201T6 cellular DNA using a B.t. "universal" forward primer and a reverse oligonucleotide primer. The sequence of the B.t. universal primer is: 5'-GGACCAGGAT TTACAGGAGG AGAT-3' (SEQ ID NO. 2). The sequence of the reverse primer is: 5'-TGGAATAAATTCAATT(C or T)(T or G)(A or G)TC(T or A)A-3' (SEQ ID NO. 3). The amplified DNA fragment was radiolabelled with $^{32}$P-dATP using a BMB (Indianapolis, Ind.) random priming kit. Southern blot analyses of PS201T6 DNA with this probe revealed hybridizing bands that included an approximately 9.3 kbp HindIII fragment and two EcoRI fragments approximately 1.8 and 4.5 kbp in size.

A gene library was constructed from PS201T6 DNA partially digested with Sau3A. Partial restriction digests were fractionated by agarose gel electrophoresis. DNA fragments 9.3 to 23 kbp in size were excised from the gel, electroeluted from the gel slice, purified on an Elutip D ion exchange column (Schleicher and Schuell, Keene, N.H.), and recovered by ethanol precipitation. The Sau3A inserts were ligated into BamHI-digested LambdaGem-11 (Promega, Madison, Wis.). Recombinant phage were packaged and plated on *E. coli* KW251 cells. Plaques were screened by hybridization with the probes described above. Hybridizing phage were plaque-purified and used to infect liquid cultures of *E. coli* KW251 cells for isolation of DNA by standard procedures (Maniatis, T., E. F. Fritsch, J. Sambrook [1982] *Molecular Cloning: A Laboratory Manual*, Cold Spring Harbor Laboratory, New York).

For subcloning the gene encoding the 30 kDa toxin gene, preparative amounts of phage DNA were digested with EcoRI and electrophoresed on an agarose gel. The approximately 4.5 kbp band containing the toxin gene was excised from the gel, electroeluted from the gel slice, and purified by anion exchange chromatography as above. The purified DNA insert was ligated into EcoRI-digested pBluescript K/S (Stratagene, La Jolla, Calif.). The ligation mix was used to transform frozen, competent *E. coli* NM522 cells (ATCC 47000). Transformants were plated on LB agar containing 100 μg/ml ampicillin, 1 mM IPTG, and 0.5 mM XGAL. Plasmids were purified from putative recombinants by alkaline lysis (Maniatis et al., supra) and analyzed by restriction endonuclease digestion and agarose gel electrophoresis. The desired plasmid construct pMYC2357 contains a toxin gene that is novel compared to other toxin genes encoding insecticidal proteins.

Sequence analysis of the toxin gene revealed that it encodes a protein of 29,906 daltons, deduced from the DNA sequence. The nucleotide and deduced amino acid sequences are shown in SEQ ID NOS. 6 and 7, respectively.

The gene encoding the 30 kDa was expressed under control of the p52A1 promoter and ribosome binding site in the vector, pBClac (an *E. coli/B. thuringiensis* shuttle vector comprised of the replication origin from pBC16 (Bernhard, K. et al. [1978] *J. Bacteriol.* 133:897–903) and pUC19 (Yanisch-Perron, C. et al. [1985] *Gene* 33:103–119). The 30 kDa open reading frame and 3' flanking sequences were amplified by PCR using a forward oligonucleotide complementary to the 5' end of the gene and a reverse oligonucleotide complementary to the T7 promoter region of pBluescript. The sequence of the gene-specific primer was: 5'-

GGAATTCCTC ATG AAA GAG TCA ATT TAC TAC A-3' (SEQ ID NO. 4). This primer contained a 5' BspHI cloning site. The p52A1 promoter/rbs sequences were amplified using a promoter-specific primer and a vector primer from pMYC2321. The sequence of promoter-specific primer was 5'-GTAAACATGT TCATACCACC TTTTTAA-3' (SEQ ID NO. 5). This primer contained a 5' AflIII cloning site. The p52A1 promoter fragment (digested with BamHI and AflIII), the 30 kDa toxin gene fragment (digested with BspHI and SalI) and pBClac (digested with BamHI and SalI) were ligated together to generate pMYC2358. This construct was introduced into the acrystalliferous (Cry−) B.t. host, CryB (A. Aronson, Purdue University, West Lafayette, Ind.) by electroporation. Expression of the 30 kDa toxin was demonstrated by SDS-PAGE analysis. NaBr-purified crystals were prepared (Pfannenstiel et al., supra).

For subcloning the 130 kDa toxin, preparative amounts of phage DNA were digested with SalI and electrophoresed on an agarose gel. The approximately 12.8 kbp band containing the toxin gene was excised from the gel, electroeluted from the gel slice, and purified by ion exchange chromatography as described above. The purified DNA insert was ligated into an XhoI-digested pHTBlueII (an E. coli/B. thuringiensis shuttle vector comprised of pBluescript S/K (Stratagene, La Jolla, Calif.) and the replication origin from a resident B.t. plasmid (Lereclus et al., supra). The ligation mix was used to transform frozen, competent E. coli NM522 cells (ATCC 47000). β-galactosidase transformants were screened by restriction digestion of alkaline lysate plasmid minipreps as above. The desired plasmid construct, pMYC2362, contains a gene encoding a 130 kDa toxin that is novel compared to other toxin genes encoding pesticidal proteins.

pMYC2362 was introduced into the acrystalliferous (Cry−) B.t. host, CryB (A. Aronson, Purdue University, West Lafayette, Ind.), by electroporation. Expression of the 130 kDa toxin was demonstrated by SDS-PAGE analysis. NaBr-purified cyrstals were prepared as above.

Example 4

Activity of B.t. Isolate PS201T6 Against House Fly Musca domestica Larvae

Twenty grams of house fly media (Bioseryc, Inc., Frenchtown, N.J.) was mixed with approximately 6 mg PS201T6 toxin crystals per 50 ml of water. Ten 1st instar larvae were placed in a plastic 6 oz. cup with the diet/toxin preparation and covered with a paper towel. The bioassay was held in an incubator at 27° C. and evaluated for puparium formation.

TABLE 3

| Toxicity of Bacillus thuringiensis crystals to the 1st instar house fly | |
|---|---|
| B.t. isolate | Percent to form puparium (S.D) |
| PS201T6 | 0% |
| Control | 97% ± 5 |

Example 5

Activity Against Housefly Adults

The B.t. isolate PS201T6 was tested against housefly adults. Gradient purified delta-endotoxin from PS201T6 was suspended in a 10% sucrose solution at a rate of 2 mg/ml. The resulting mixture was used to saturate a dental wick placed in a clear plastic cup. Ten flies were added to the cup. Mortality was assessed 24 hours post-treatment. PS201T6 caused 100% mortality to the house fly, Musca domestica. Control experiments using water showed no mortality.

Example 6

Activity of B.t. Isolates Against Aedes aegypti

Aedes aegypti, the yellow fever mosquito, is used as an indicator of mosquito activity. The bioassay is performed on a spore and crystal suspension or a suspension of purified crystals. Dilutions of the suspension are added to water in a small cup. Third instar larvae are added, and mortality is read after 48 hours.

The B.t. isolates, PS201T6, PS201L1, PS196S1, and PS92 were each active against Aedes aegypti.

Example 7

Activity of B.t Isolates to Leafminers

The B.t. isolates, PS201T6, PS201L1, PS196S1, and PS92J, were grown using standard techniques. Second instar larvae were allowed to feed on broths ad lib. All four isolates were toxic to the leafminer, Liriomyza trifoli.

Bioassay conditions were created to assess the affect of the purified 30 kDa toxin from PS201T6 on the mining ability and mortality rate of leafmining flies. Samples were evaluated after a 48 hour incubation. The results are shown in Table 4.

TABLE 4

| Purified protein from B.t. isolate PS201T6 Reduces Mining activity of Dipteran Leafminers Liriomyza trifoli | | | |
|---|---|---|---|
| Toxin | | Average % Mortality (3 assays) | Average % Active Miners (2 assays) |
| 201T6 | 1 mg/ml | 81 | 9 |
| 201T6 | .1 mg/ml | 71 | 10 |
| 201T6 | .01 mg/ml | 59 | 26 |
| control | — | 5 | 69 |

Fresh cultures of PS201T6 contacted with leafminers (Liriomyza trifoli) yielded an average mortality rate of 97%.

Example 8

Pronase Processing of PS201T6 Culture Material

Pronase is a commercially-available enzyme preparation which can be used to proteolytically degrade B.t. toxin compositions to assess the activity of toxin fragments. The 133 kDa protein from PS201T6 was hydrolyzed to low molecular weight peptides. Surprisingly, the 30 kDa toxin from PS201T6 was digested to a limit peptide of approximately 25 kDa after Pronase treatment as described herein.

Cultures of PS201T6 were harvested by centifugation and resuspended in about 1/9th to 1/25th of their original culture volume in 0.1M $Na_2CO_3$/$NaHCO_3$ (pH 11.0) containing 0.5 mg/ml Pronase E (Sigma Chemical Company, P-5147 type XIV bacterial Protease from Streptomyces griseus). The suspension was incubated at 37° C. overnight with mixing. Suspensions were dialyzed against 2 changes of 50 to 100 volumes each of either distilled water or 0.1M $Na_2CO_3$/$NaHCO_3$ (pH 9.5) to yield dialyzed suspensions.

The suspension resulting from the 0.1M $Na_2CO_3$/$NaHCO_3$ (pH 9.5) dialysis was centrifuged to remove cells, spores and debris. Additional purification from spores and debris was accomplished by filtration through Whatman glass microfibre filters, 0.8 micron cellulose acetate filters and 0.2 micron cellulose acetate filters to yield a filtered supernatant.

Dialyzed suspensions and filtered supernatants can be further dialyzed against 2 changes of 50 to 100 volumes distilled water, followed by lyophilization to yield lyophilized samples.

When the dialyzed suspension, filtered supernatant and lyophilized samples of Pronase-treated toxin materials were supplied to adult houseflies in 10% sucrose solutions on dental wicks, each was lethal to the flies. $LC_{50}$ values of these materials ranged from 40 to 300 micrograms per ml based on the activated polypeptide content.

Example 9

Activated Toxins from PS201T6

The removal of 43 amino acids from the N-terminus of the 201T6 30 kDa toxin was found to result in an advantageous activation of this toxin which increased the scope and potency of its activity. The sequence of the truncated toxin is shown in SEQ ID NO. 8. Table 5 compares the physical properties of the truncated toxin and the full length 30 kDa toxin.

TABLE 5

| | 201T6 - 30 kDa | Activated 201T6 - 25 kDa |
|---|---|---|
| Molecular Weight | 29,906 | 24,782 |
| Isolectric Point | 4.92 | 4.91 |
| Extinction Coefficient | 26,150 | 21,680 |

Further, the removal of about 1 to about 12 additional amino acids from the N-terminus can also be done to obtain an activated toxin. It is also possible to remove about 5 to about 10 amino acids from the C-terminus.

Example 10

Activity Against Corn Rootworm

A toxin-containing suspension of B.t. PS201T6 was dispensed onto the surface of an agar based insect diet. Excess liquid was evaporated from the surface before transferring neonate Western Corn Rootworm (WCR: *Diabrotica virgifera virgifera*) onto the diet. In three days, an estimated rate of 45 μg toxin per $cm^2$ caused 90% mortality of the WCR larvae. Control mortality from exposure to water only was less than 15%.

Example 11

Insertion of Toxin Genes Into Plant Cells

One aspect of the subject invention is the transformation of plant cells with genes encoding a dipteran or corn rootworm-active toxin. The transformed plant cells are resistant to attack by dipteran or corn rootworm pests.

Genes encoding toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the B.t. toxin can be inserted into the vector at a suitable restriction site. The resulting plasmid is used for transformation into *E. coli* The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al. (1985) EMBO J. 4:277–287.

Once the inserted DNA has been integrated in the genome, it is relatively stable there and, as a rule, does not excise. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the virus region necessary for the transfer of the T-DNA. Intermediate vectors cannot replicate themselves in agrobacteria. The intermediate vector can be transferred into *Agobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] *Mol. Gen. Genet.* 163:181–187). The agrobacterium used as a host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed traits to progeny plants. Such plants can be grown in the normal manner and crossed with plants that have the same transformed hereditary factors or other hereditary factors. The resulting hybrid individuals have the corresponding phenotypic properties.

Example 12

Cloning of Novel B.t. Genes Into Insect Viruses

A number of viruses are known to infect insects. These viruses include, for example, baculoviruses and entomopoxviruses. In one embodiment of the subject invention, dipteran and/or coleopteran-active genes, as described herein, can be placed with the genome of the insect virus, thus enhancing the pathogenicity of the virus. Methods for constructing insect viruses which comprise B.t. toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee [1990] *J. Gen. Virol.* 71:1535–1544) and Martens et al. (Martens, J. W. M., G. Honee, D. Zuidema, J. W. M. van Lent, B. Visser, J. M. Vlak [1990] *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 39 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:1:

GACTGGATCC ATGAAAGAAW SWATWTATTA TAATGAAG      39

( 2 ) INFORMATION FOR SEQ ID NO:2:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

GGACCAGGAT TTACAGGAGG AGAT      24

( 2 ) INFORMATION FOR SEQ ID NO:3:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

TGGAATAAAT TCAATTYKRT CWA      23

( 2 ) INFORMATION FOR SEQ ID NO:4:

( i ) SEQUENCE CHARACTERISTICS:
        ( A ) LENGTH: 31 bases
        ( B ) TYPE: nucleic acid
        ( C ) STRANDEDNESS: single -continued (D) TOPOLOGY: linear (ii) MOLECULE TYPE: DNA (synthetic)

(xi) SEQUENCE DESCRIPTION: SEQ ID NO:4:

GGAATTCCTC ATGAAAGAGT CAATTTACTA C  31

(2) INFORMATION FOR SEQ ID NO:5:

(i) SEQUENCE CHARACTERISTICS:
      (A) LENGTH: 27 bases
      (B) TYPE: nucleic acid
      (C) STRANDEDNESS: single
      (D) TOPOLOGY: linear (ii) MOLECULE TYPE: DNA (synthetic)

(xi) SEQUENCE DESCRIPTION: SEQ ID NO:5:

GTAAACATGT TCATACCACC TTTTTAA  27

(2) INFORMATION FOR SEQ ID NO:6:

(i) SEQUENCE CHARACTERISTICS:
      (A) LENGTH: 795 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Bacillus thuringiensis
      (B) STRAIN: neoleoensis
      (C) INDIVIDUAL ISOLATE: PS201T6

(vii) IMMEDIATE SOURCE:
      (A) LIBRARY: LambdaGem (TM)-11 library of Kenneth E. Narva
      (B) CLONE: 201T635

(xi) SEQUENCE DESCRIPTION: SEQ ID NO:6:

| | | | | | |
|---|---|---|---|---|---|
| ATGAAAGAGT | CAATTTACTA | CAATGAAGAA | AATGAAATAC | AAATTTCACA | AGGAAACTGT | 60 |
| TTCCCAGAAG | AATTAGGACA | TAATCCTTGG | AGACAACCTC | AATCCACAGC | AAGAGTTATT | 120 |
| TATTTAAAAG | TAAAAGATCC | TATTGATACT | ACTCAATTAT | TAGAAATAAC | AGAAATCGAA | 180 |
| AATCCCAATT | ATGTATTACA | AGCTATTCAA | CTAGCTGCTG | CCTTCCAAGA | TGCATTAGTA | 240 |
| CCAACTGAAA | CAGAATTTGG | AGAAGCCATT | AGATTTAGTA | TGCCTAAAGG | ATTAGAAGTT | 300 |
| GCAAAAACTA | TTCAACCTAA | GGGTGCTGTT | GTTGCTTACA | CAGATCAAAC | TCTGTCACAA | 360 |
| AGCAACAACC | AAGTTAGTGT | TATGATTGAT | AGAGTTATTA | GTGTTTTAAA | AACTGTAATG | 420 |
| GGAGTAGCTC | TTAGTGGTTC | CATTATAACT | CAATTAACAG | CTGCTATCAC | TGATACTTTT | 480 |
| ACAAACCTTA | ATACACAAAA | AGATTCTGCT | TGGGTTTTTT | GGGGAAAAGA | AACTTCACAT | 540 |
| CAAACAAATT | ACACATATAA | TGTCATGTTT | GCAATTCAAA | ATGAAACAAC | TGGACGCGTA | 600 |
| ATGATGTGTG | TACCTATTGG | ATTTGAAATT | AGAGTATTTA | CTGATAAAAG | AACAGTTTTA | 660 |
| TTTTTAACAA | CTAAAGATTA | CGCTAATTAT | AGTGTGAATA | TTCAAACCCT | AAGGTTTGCT | 720 |
| CAACCACTTA | TTGATAGCAG | AGCACTTTCA | ATTAATGATT | TATCAGAAGC | ACTTAGATCT | 780 |
| TCTAAATATT | TATAC | | | | | 795 |

(2) INFORMATION FOR SEQ ID NO:7:

(i) SEQUENCE CHARACTERISTICS:
      (A) LENGTH: 265 amino acids (B) TYPE: amino acid
(C) STRANDEDNESS: single
(D) TOPOLOGY: linear (ii) MOLECULE TYPE: protein (iii) HYPOTHETICAL: YES (iv) ANTI-SENSE: NO (vi) ORIGINAL SOURCE:
(A) ORGANISM: Bacillus thuringiensis
(B) STRAIN: neoleoensis
(C) INDIVIDUAL ISOLATE: PS201T6

(vii) IMMEDIATE SOURCE:
(A) LIBRARY: LambdaGem (TM)-11 Library of Kenneth E. Narva
(B) CLONE: 201T635

(xi) SEQUENCE DESCRIPTION: SEQ ID NO:7:

```
Met Lys Glu Ser Ile Tyr Tyr Asn Glu Glu Asn Glu Ile Gln Ile Ser
1               5                   10                  15

Gln Gly Asn Cys Phe Pro Glu Glu Leu Gly His Asn Pro Trp Arg Gln
            20                  25                  30

Pro Gln Ser Thr Ala Arg Val Ile Tyr Leu Lys Val Lys Asp Pro Ile
        35                  40                  45

Asp Thr Thr Gln Leu Leu Glu Ile Thr Glu Ile Glu Asn Pro Asn Tyr
    50                  55                  60

Val Leu Gln Ala Ile Gln Leu Ala Ala Ala Phe Gln Asp Ala Leu Val
65                  70                  75                  80

Pro Thr Glu Thr Glu Phe Gly Glu Ala Ile Arg Phe Ser Met Pro Lys
                85                  90                  95

Gly Leu Glu Val Ala Lys Thr Ile Gln Pro Lys Gly Ala Val Val Ala
            100                 105                 110

Tyr Thr Asp Gln Thr Leu Ser Gln Ser Asn Asn Gln Val Ser Val Met
        115                 120                 125

Ile Asp Arg Val Ile Ser Val Leu Lys Thr Val Met Gly Val Ala Leu
    130                 135                 140

Ser Gly Ser Ile Ile Thr Gln Leu Thr Ala Ala Ile Thr Asp Thr Phe
145                 150                 155                 160

Thr Asn Leu Asn Thr Gln Lys Asp Ser Ala Trp Val Phe Trp Gly Lys
                165                 170                 175

Glu Thr Ser His Gln Thr Asn Tyr Thr Tyr Asn Val Met Phe Ala Ile
            180                 185                 190

Gln Asn Glu Thr Thr Gly Arg Val Met Met Cys Val Pro Ile Gly Phe
        195                 200                 205

Glu Ile Arg Val Phe Thr Asp Lys Arg Thr Val Leu Phe Leu Thr Thr
    210                 215                 220

Lys Asp Tyr Ala Asn Tyr Ser Val Asn Ile Gln Thr Leu Arg Phe Ala
225                 230                 235                 240

Gln Pro Leu Ile Asp Ser Arg Ala Leu Ser Ile Asn Asp Leu Ser Glu
                245                 250                 255

Ala Leu Arg Ser Ser Lys Tyr Leu Tyr
            260                 265
```

(2) INFORMATION FOR SEQ ID NO:8:

(i) SEQUENCE CHARACTERISTICS:
(A) LENGTH: 222 amino acids
(B) TYPE: amino acid
(C) STRANDEDNESS: single
(D) TOPOLOGY: linear (ii) MOLECULE TYPE: protein ( i i i ) HYPOTHETICAL: YES ( i v ) ANTI-SENSE: NO ( v i ) ORIGINAL SOURCE:
    ( A ) ORGANISM: Bacillus thuringiensis
    ( B ) STRAIN: neoleoensis
    ( C ) INDIVIDUAL ISOLATE: P ( i ) SEQUENCE CHARACTERISTICS:
    ( A ) LENGTH: 29 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:10:

ATGAAAGAA W  S W AT W TATTA  TATTGAAGA            29

We claim:

1. An isolated polynucleotide sequence comprising DNA wherein said DNA encodes a toxin which is active against *Aedes aegypti* and wherein said DNA is from *Bacillus thuringiensis* isolate PS201T6, and wherein said toxin has a molecular weight of from about 25 kD to about 30 kD.

2. The polynucleotide sequence, according to claim 1, comprising DNA encoding SEQ ID NO. 7.

3. The polynucleotide sequence, according to claim 1, comprising DNA having SEQ ID NO. 6.

4. The polynucleotide sequence, according to claim 2, encoding the amino acid sequence shown in SEQ ID NO. 8.

5. A recombinant DNA transfer vector comprising the polynucleotide of claim 1.

6. A method for the control of corn rootworm which comprises administering to said corn rootworm, or its environment, an effective amount of *Bacillus thuringiensis* isolate PS201T6 or spores or a toxin from said isolate.

7. The method, according to claim 6, wherein said toxin comprises the amino acid sequence shown in SEQ ID NO. 7.

8. The method, according to claim 7, wherein said toxin comprises the amino acid sequence shown in SEQ ID NO. 8.

* * * * *

UNITED STATES PATENT AND TRADEMARK OFFICE
CERTIFICATE OF CORRECTION

PATENT NO. : 5,436,002
DATED : July 25, 1995
INVENTOR(S) : Jewel Payne, Kenneth E. Narva, Kendrick A. Uyeda, Christine J. Stalder, Tracy E. Michaels It is certified that error appears in the above-indentified patent and that said Letters Patent is hereby corrected as shown below:

Column 1, line 13: Delete "07/547,399" and insert --07/647,399--.

Column 2, line 6: Delete "CryIII" and insert --CryIII--

Column 3, line 8: Delete "Museidae" and insert --Muscidae--.

Column 4, lines 4-5: Delete "in the soft." and insert --in the soil.--

Column 7, line 67: Delete "in the an" and insert --in the art--.

Column 8, line 28: Delete "toms" and insert --toxins--.

Column 8, line 60: Delete "Leu, De" and insert --Leu, Ile--.

Column 14, line 14: Delete "HindlII" and insert --HindIII--.

Column 18, line 42: Delete "the virus region" and insert --the vir region--.

Signed and Sealed this

Thirty-first Day of October 1995

Attest:

BRUCE LEHMAN

Attesting Officer

Commissioner of Patents and Trademarks